United States Patent
De Klerk et al.

(10) Patent No.: US 11,834,393 B2
(45) Date of Patent: Dec. 5, 2023

(54) ORGANIC COMPOUNDS HAVING TASTE-MODIFYING PROPERTIES

(71) Applicant: GIVAUDAN SA, Vernier (CH)

(72) Inventors: Adri De Klerk, Made (NL); Cornelis Winkel, Bussum (NL)

(73) Assignee: GIVAUDAN SA, Vernier (CH)

( * ) Notice: Subject to any disclaimer, the term of this patent is extended or adjusted under 35 U.S.C. 154(b) by 5 days.

(21) Appl. No.: 17/157,522

(22) Filed: Jan. 25, 2021

(65) Prior Publication Data

US 2021/0147345 A1    May 20, 2021

Related U.S. Application Data

(63) Continuation of application No. 14/916,846, filed as application No. PCT/EP2013/070540 on Oct. 2, 2013, now abandoned.

(51) Int. Cl.
| | | |
|---|---|---|
| *C07C 237/16* | (2006.01) | |
| *C07C 237/06* | (2006.01) | |
| *C07C 323/60* | (2006.01) | |
| *C07C 233/58* | (2006.01) | |
| *A23L 27/20* | (2016.01) | |
| *A23L 27/00* | (2016.01) | |
| *C07C 323/04* | (2006.01) | |
| *C07D 207/16* | (2006.01) | |
| *C07C 323/41* | (2006.01) | |

(52) U.S. Cl.
CPC .......... *C07C 237/16* (2013.01); *A23L 27/202* (2016.08); *A23L 27/203* (2016.08); *A23L 27/204* (2016.08); *A23L 27/2022* (2016.08); *A23L 27/2054* (2016.08); *A23L 27/88* (2016.08); *C07C 233/58* (2013.01); *C07C 237/06* (2013.01); *C07C 323/41* (2013.01); *C07C 323/60* (2013.01); *C07D 207/16* (2013.01); *A23V 2002/00* (2013.01)

(58) Field of Classification Search
CPC ... C07C 237/16; C07C 233/58; C07C 237/06; C07C 323/41; C07C 323/60; A23L 27/2054; A23L 27/88; A23L 27/203; A23L 27/204; A23L 27/2022; A23L 27/202; C07D 207/16; A23V 2002/00
USPC ......................................... 426/535, 534, 650
See application file for complete search history.

(56) References Cited

U.S. PATENT DOCUMENTS

| | | | |
|---|---|---|---|
| 2,835,590 A | 5/1958 | Rusoff et al. | |
| 3,024,272 A | 3/1962 | Archibald et al. | |
| 3,624,114 A | 11/1971 | Morelle | |
| 3,801,633 A | 4/1974 | Toyoshima et al. | |
| 3,878,305 A | 4/1975 | Damico et al. | |
| 3,940,500 A | 2/1976 | Sortwell, III | |
| 3,947,589 A | 3/1976 | Misato et al. | |
| 4,016,287 A | 4/1977 | Eberhardt et al. | |
| 4,066,799 A | 1/1978 | Cornelius et al. | |
| 4,093,740 A | 6/1978 | Fahnenstich et al. | |
| 4,248,859 A | 2/1981 | Roswell et al. | |
| 4,442,090 A | 4/1984 | Kakeya et al. | |
| 4,448,785 A | 5/1984 | Kathawala et al. | |
| 4,479,974 A | 10/1984 | Schenz | |
| 4,757,066 A | 7/1988 | Shiokari et al. | |
| 4,777,195 A | 10/1988 | Hesse et al. | |
| 5,164,414 A | 11/1992 | Vincent et al. | |
| 5,176,934 A | 1/1993 | Lee | |
| 5,286,480 A | 2/1994 | Boggs et al. | |
| 5,312,831 A | 5/1994 | Ayral-Kaloustian et al. | |
| 5,780,090 A | 7/1998 | Frerot et al. | |
| 6,251,931 B1 | 6/2001 | Boger et al. | |
| 7,320,807 B2 | 1/2008 | Asher et al. | |

(Continued)

FOREIGN PATENT DOCUMENTS

| | | |
|---|---|---|
| AU | 675778 | 2/1997 |
| CN | 101597239 A | 12/2009 |

(Continued)

OTHER PUBLICATIONS

J. P. Ley, "Masking Bitter Taste by Molecules", Chemical Perception, 2008, vol. 1, pp. 58-77.
C. Ma, et al., "Effect of Fatty N-Acylamino Acids on Some Functional Properties of Two Food Proteins", J. Agrig Food 1993, vol. 41, pp. 1182-1188.
A. Paquet, "Preparation of some long-chain N-acyl derivatives of essential amino acids for nutrition studies", Journal Biochem., vol. 58, National Research Council of Canada, pp. 573-576, 1980.
M. Gerova, et al., "Self-assembly properties of some chiral N-Palmitoyl amino acid surfactants in aqueous solution", Journal of Colloid and Interface Science, 2008, vol. 319, pp. 526-533.

(Continued)

*Primary Examiner* — Leslie A Wong
(74) *Attorney, Agent, or Firm* — Norris McLaughlin PA

(57) ABSTRACT

This disclosure relates to flavour modification and to compounds of formula (I) or edible salts thereof,

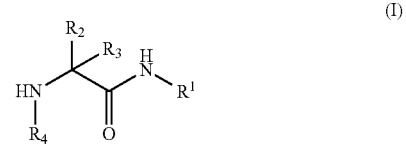

(I)

wherein
$R^1$ is selected from $C_6$-$C_{20}$ alkyl, and $C_9$-$C_{25}$ alkenyl, and
  i) $R^3$ and $R^4$ are hydrogen and $R^2$ the residue of a proteinogenic amino acid;
  ii) $R^2$ and $R^3$ are methyl and $R^4$ is hydrogen; or $R^4$ is hydrogen and $R^2$ and $R^3$ form together with the carbon atom to which they are attached cyclopropyl;
  iii) $R^2$ is hydrogen, and $R^3$ and $R^4$ together are —$CH_2$—$CH_2$—$CH_2$— useful in modifying flavours.

14 Claims, No Drawings

(56) References Cited

U.S. PATENT DOCUMENTS

| | | | |
|---|---|---|---|
| 7,981,457 | B2 | 7/2011 | Visser et al. |
| 8,778,437 | B2 | 7/2014 | Renes et al. |
| 8,828,469 | B2 | 9/2014 | Langer et al. |
| 8,945,651 | B2 | 2/2015 | Visser et al. |
| 9,560,846 | B2 | 2/2017 | Riera et al. |
| 9,560,876 | B2 | 2/2017 | Riera et al. |
| 2001/0002257 | A1 | 5/2001 | Stolz |
| 2001/0014695 | A1 | 8/2001 | Behl et al. |
| 2004/0081708 | A1 | 4/2004 | Baxter |
| 2004/0157932 | A1 | 8/2004 | Saebo |
| 2005/0031789 | A1 | 2/2005 | Liu et al. |
| 2007/0282002 | A1 | 12/2007 | Maezono et al. |
| 2008/0038428 | A1 | 2/2008 | Visser et al. |
| 2008/0038429 | A1 | 2/2008 | Visser et al. |
| 2008/0038430 | A1 | 2/2008 | Visser et al. |
| 2008/0050500 | A1 | 2/2008 | Muranishi et al. |
| 2009/0057618 | A1 | 3/2009 | Leinweber et al. |
| 2011/0081473 | A1 | 4/2011 | Hamasaki et al. |
| 2013/0022728 | A1 | 1/2013 | Popplewell et al. |
| 2015/0044332 | A1 | 2/2015 | Shi et al. |
| 2015/0044347 | A1 | 2/2015 | Shi et al. |
| 2015/0050408 | A1 | 2/2015 | Shi et al. |
| 2015/0064326 | A1 | 3/2015 | Shi et al. |
| 2015/0064327 | A1 | 3/2015 | Shi et al. |
| 2015/0072060 | A1 | 3/2015 | Shi et al. |
| 2015/0086694 | A1 | 3/2015 | Shi et al. |

FOREIGN PATENT DOCUMENTS

| | | |
|---|---|---|
| CN | 102028176 A | 4/2011 |
| CN | 102036571 B | 7/2013 |
| DE | 2234399 | 1/1974 |
| EP | 0030448 B1 | 4/1985 |
| EP | 0198348 A2 | 10/1986 |
| EP | 0208279 A1 | 1/1987 |
| EP | 0271816 A2 | 12/1987 |
| EP | 0356784 A2 | 3/1990 |
| EP | 0432039 A2 | 6/1991 |
| EP | 0443891 A1 | 8/1991 |
| EP | 0460566 A2 | 12/1991 |
| EP | 0500332 A2 | 8/1992 |
| EP | 0891764 A1 | 1/1999 |
| EP | 1263286 | 12/2002 |
| EP | 1356744 A1 | 10/2003 |
| EP | 1471052 A1 | 10/2004 |
| EP | 1520850 A2 | 4/2005 |
| EP | 1637042 A1 | 3/2006 |
| EP | 2031092 A2 | 3/2009 |
| EP | 2058297 A1 | 5/2009 |
| EP | 2119373 A1 | 11/2009 |
| EP | 2140770 A1 | 1/2010 |
| EP | 2184051 A1 | 5/2010 |
| EP | 2382871 A1 | 11/2011 |
| EP | 2597082 A1 | 5/2013 |
| FR | 1603799 A | 5/1971 |
| FR | 2765109 A1 | 12/1998 |
| FR | 2878439 | 6/2006 |
| GB | 1130480 | 10/1968 |
| GB | 1426545 | 9/1973 |
| GB | 1377271 | 12/1974 |
| GB | 1436614 | 5/1976 |
| GB | 1560000 | 1/1980 |
| GB | 2200633 A | 8/1988 |
| JP | 34614357 Y1 | 5/1971 |
| JP | S4614357 Y1 | 5/1971 |
| JP | S4985244 A | 8/1974 |
| JP | S49124244 | 11/1974 |
| JP | 52-94453 A | 8/1977 |
| JP | S53118516 A | 10/1978 |
| JP | 5690046 | 7/1981 |
| JP | S56123910 A | 9/1981 |
| JP | S56131365 A | 10/1981 |
| JP | S63156849 A | 6/1988 |
| JP | S63218649 A | 9/1988 |
| JP | H2256608 A | 10/1990 |
| JP | H06157440 A | 6/1994 |
| JP | H08103242 | 4/1996 |
| JP | H08103242 A | 4/1996 |
| JP | H08208453 A | 8/1996 |
| JP | 9313129 A | 12/1997 |
| JP | 2824158 B2 | 11/1998 |
| JP | 2006296356 A | 11/2006 |
| JP | 201229616 A | 2/2012 |
| RU | 2335926 C1 | 10/2008 |
| WO | 8603944 | 7/1986 |
| WO | 8701935 A1 | 4/1987 |
| WO | 9738688 A1 | 10/1997 |
| WO | 0057726 A1 | 10/2000 |
| WO | 01030143 A2 | 5/2001 |
| WO | 0159067 A2 | 8/2001 |
| WO | 02094764 A1 | 11/2002 |
| WO | 0334842 A1 | 5/2003 |
| WO | 2004000787 A2 | 12/2003 |
| WO | 2004075663 | 9/2004 |
| WO | 2005096843 A1 | 10/2005 |
| WO | 2005096844 A1 | 10/2005 |
| WO | 2005102071 A1 | 11/2005 |
| WO | 2006009425 A1 | 1/2006 |
| WO | 2006010590 A1 | 2/2006 |
| WO | 2006046853 A1 | 5/2006 |
| WO | 2008040756 A1 | 4/2008 |
| WO | 2009021558 A1 | 2/2009 |
| WO | 2009141294 | 11/2009 |
| WO | 2009141294 A1 | 11/2009 |
| WO | 2010022914 A1 | 3/2010 |
| WO | 2011141685 A2 | 5/2011 |
| WO | 2011105985 A1 | 9/2011 |
| WO | 2011141685 A2 | 11/2011 |
| WO | 2012071293 A2 | 5/2012 |
| WO | 2013010991 A1 | 1/2013 |
| WO | 2013148991 A1 | 10/2013 |
| WO | 2013148997 | 10/2013 |
| WO | 2013149008 A2 | 10/2013 |
| WO | 2013149012 | 10/2013 |
| WO | 2013149019 | 10/2013 |
| WO | 2013149022 | 10/2013 |
| WO | 2013149025 | 10/2013 |
| WO | 2013149031 A2 | 10/2013 |
| WO | 2013149035 A2 | 10/2013 |

OTHER PUBLICATIONS

R. Damico, "An Investigation of N-Substituted Methionine Derivatives for Food Supplementation", J. Agr.Food vol. 23, No. 1, pp. 30-33, 1975.
English translation of first Japanese Office Action for corresponding application JP 2015-503564 dated Dec. 15, 2016.
Written Opinion of the Intellectual Property Office of Singapore for corresponding application CN 11201405104P dated May 30, 2016.
English translation of second Chinese Office Action for corresponding application CN 201380017898.7 dated May 3, 2016.
English translation of first Japanese Office Action for corresponding application JP 2015-503572 dated Dec. 15, 2016.
English translation of second Chinese Office Action for corresponding application CN 201380017847.4 dated May 5, 2016.
English translation of third Chinese Office Action for corresponding application CN 201380017847.4 dated Nov. 2016.
English translation of first Japanese Office Action for corresponding application JP 2015-503573 dated Dec. 14, 2016.
English translation of second Chinese Office Action for corresponding application CN 201380017924.6 dated May 31, 2016.
English translation of first Japanese Office Action for corresponding application JP 2015-503577 dated Jan. 4, 2017.
English translation of first Japanese Office Action for corresponding application JP 2015-503584 dated Jan. 27, 2017.
English translation of first Japanese Office Action for corresponding application JP 2015-503579 dated Oct. 14, 2016.
English translation of second Chinese Office Action for corresponding application CN 201380017825.8 dated May 31, 2016.
English translation of second Chinese Office Action for corresponding application CN 201380017814.x dated April 1, 2016.

(56) References Cited

OTHER PUBLICATIONS

English translation of second Chinese Office Action for corresponding application CN 201380017832.8 dated Mar. 2016.
English translation of second Chinese Office Action for corresponding application CN 201380017831.3 dated Mar. 2, 2016.
Written Opinion of the Intellectual Property Office of Singapore for corresponding application CN 11201405188X dated Sep. 13, 2016.
Written Opinion of the Intellectual Property Office of Singapore for corresponding application CN 11201405295W dated Apr. 15, 2016.
Written Opinion of the Intellectual Property Office of Singapore for corresponding application CN 11201405409P dated May 11, 2016.
Written Opinion of the Intellectual Property Office of Singapore for corresponding application CN 11201405340X dated Mar. 24, 2016.
Written Opinion of the Intellectual Property Office of Singapore for corresponding application CN 112014053 dated Mar. 23, 2016.
Written Opinion of the Intellectual Property Office of Singapore for corresponding application CN 11201601652X dated Sep. 22, 2016.
Second International Search Report for corresponding application PCT/US2013/034355 dated Oct. 7, 2013.
Second International Search Report for corresponding application PCT/US2013/034299 dated Sep. 27, 2013.
Second International Search Report for corresponding application PCT/US2013/034342 dated Jul. 12, 2013.
International Preliminary Report on Patentability for corresponding application PCT/US2013/034342 dated Oct. 1, 2014.
Written Opinion of the International Searching Authority for corresponding application PCT/US2013/034342 dated Jul. 12, 2013.
Second International Search Report for corresponding application PCT/US2013/034395 dated Nov. 18, 2013.
Second International Search Report for corresponding application PCT/US2013/034403 dated Nov. 6, 2013.
B. Tan, et al., "Identification of endogenous acyl amino acids based on a targeted lipidomics approach", Journal of Research, vol. 51, pp. 112-119, 2010.
Written Opinion of the Intellectual Property Office of Singapore for corresponding application CN 11201405413S dated Jun. 24, 2016.
Hession, "N-Acetylglutamate and N-Acetylaspartate in Soybeans (*Glycine max* L.), Maize (*Zea maize* L.), and Other Foodstuffs", Journal of Agricultural and Food Chemistry, 2008, 56, pp. 9121-9126.
Cameron, "13 Foods with Natural Umami", Readers Digest, (first posted on internet Aug. 3, 2010; downloaded May 28, 2016,from the site: http://www.rd.com/food/recipes-cooking/13-foods-with-natural-umami/) at pp. 1-5.
Doving, et al, "Chemical Senses and Flavour", D. Reidel Publishing Company, vol. 1, No. 4, Oct. 1975, pp. 387-401, USA.
Stenner, "Umami—The Science, Ingredients, and Cooking with the 'Fifth-taste'", published Dec. 11, 2009, downloaded from site: http://www.tulsafood.com/uncategorized/umami-the-science-ingredients-cooking-with-the-fifth-taste, 9 pages.
Kazda, "Sliced Cucumber and Tomato Salad from Life's Ambrosia", copyright 2009, downloaded May 28, 2016 from site: http://www.lifesambrosia.com/print-recipe/?pid=2064.
Umami Information Center/Umami Rich Foods, downloaded May 28, 2016; screen shot from Wayback Machine, dated May 5, 2011; from the site: http://www.umamiinfo.com/2011/03/umami-rich-food-vegetables.php ; 3 pages.
Roudot-Algaron, "Flavor Constituents of Aqueous Fraction Extracted from Comte Chees by Liquid Carbon Dioxide", Journal of Food Science, vol. 58, No. 5, 1993, pp. 1005-1009.
Umami Information center Web Page/Overview, first posted on the internet on Apr. 30, 2011, as found on the Internet ArchivelWayback Machine at http://www.web.archive.org/web/2011 0430102741/ http://www.umamiinfo.com/umami-rich-food/ .
International Search Report for corresponding application PCT/EP2013/070534 dated Aug. 11, 2014.
Written Opinion of the International Searching Authority for corresponding application PCT/EP2013/070534 dated Aug. 11, 2014.
International Search Report for corresponding application PCT/EP2013/070540 dated Nov. 10, 2014.
International Search Report for corresponding application PCT/EP2014/071021 dated Oct. 12, 2014.
Written Opinion of the International Searching Authority for corresponding application PCT/EP2014/071021 dated Oct. 12, 2014.
International Search Report for corresponding application PCT/EP2014/071056 dated Dec. 12, 2014.
International Search Report for corresponding application PCT/US2013/034299 dated Sep. 27, 2013.
Written Opinion of the International Searching Authority for corresponding application PCT/US2013/034299 dated Sep. 27, 2013.
International Search Report for corresponding application PCT/US2013/034335 dated Jul. 12, 2013.
Written Opinion of the International Searching Authority for corresponding application PCT/US2013/034335 dated Jul. 12, 2013.
International Search Report for corresponding application PCT/US2013/034375 dated Jul. 15, 2013.
Written Opinion of the International Searching Authority for corresponding application PCT/US2013/034375 dated Jul. 15, 2013.
International Preliminary Report on Patentability for corresponding application PCT/US2013/034375 dated Oct. 1, 2014.
International Search Report for corresponding application PCT/US2013/034388 dated Jul. 19, 2013.
Written Opinion of the International Searching Authority for corresponding application PCT/US2013/034388 dated Jul. 19, 2013.
International Preliminary Report on Patentability for corresponding application PCT/US2013/034388 dated Oct. 1, 2014.
International Search Report for corresponding application PCT/US2013/062966 dated Sep. 17, 2014.
International Search Report for corresponding application PCT/US2013/062993 dated Jun. 5, 2014.
International Search Report for corresponding application PCT/US2013/063008 dated Aug. 19, 2014.
International Search Report for corresponding application PCT/US2013/063014 dated Aug. 6, 2014.
International Search Report for corresponding application PCT/US2013/034355 dated Oct. 7, 2013.
Written Opinion of the International Searching Authority for corresponding application PCT/US2013/034355 dated Oct. 7, 2013.
International Preliminary Report on Patentability for corresponding application PCT/US2013/034355 dated Oct. 1, 2014.
Written Opinion of the International Searching Authority for corresponding application PCT/US2013/034363 dated Jul. 18, 2013.
International Preliminary Report on Patentability for corresponding application PCT/US2013/034363 dated Oct. 1, 2014.
International Search Report for corresponding application PCT/US2013/034363 dated Jul. 18, 2013.
International Search Report for corresponding application PCT/US2013/034378 dated Jul. 12, 2013.
Written Opinion of the International Searching Authority for corresponding application PCT/US2013/034378 dated Jul. 12, 2013.
International Preliminary Report on Patentability for corresponding application PCT/US2013/034378 dated Oct. 1, 2014.
International Search Report for corresponding application PCT/US2013/034395 dated Nov. 18, 2013.
Written Opinion of the International Searching Authority for corresponding application PCT/US2013/034395 dated Nov. 18, 2013.
International Preliminary Report on Patentability for corresponding application PCT/US2013/034395 dated Oct. 1, 2014.
International Search Report for corresponding application PCT/US2013/034403 dated Nov. 6, 2013.
Written Opinion of the International Searching Authority for corresponding application PCT/US2013/034403 dated Nov. 6, 2013.
International Preliminary Report on Patentability for corresponding application PCT/US2013/034403 dated Oct. 1, 2014.
T. Amagata, et al., "Gymnastatins F-H, Cytostatic Metabolites from the Sponge-Derived Fungus Gymnascella dankaliensis", American Chemical Society and American Society of Pharmacognosy, vol. 69, pp. 1384-1388, 2006.
"Aromat", Wikipedia, the free encyclopedia, http://en.wikipedia.org/wiki/Aromat.
S. H. Burstein, et al., "Potential anti-inflammatory actions of the elmiric (lipoamino) acids", Bioorganic & Medicinal Chemistry, vol. 15, pp. 3345-3355, 2007.

(56) References Cited

OTHER PUBLICATIONS

G.M. Dumowchik, et al., "The in vitro effects of Three Lysosomotropic Detergents Against Three Human Tumor Cell Lines", Bioorganic & Medicinal Chemisty Letters, vol. 5, No. 8, pp. 893-898, 1995, Great Britain.

M. Fieser, et al., "Synthetic Emulsify Agents", Chemical Laboratory of Harvord University, pp. 2825-2832, Jun. 20, 1956.

S. N. Georgiades, et al., "Synthetic libraries of tyrosine-derived bacterial metabolites", Bioorganic & Medicinal Chemisty Letters, vol. 18, pp. 3117-3121, 2008.

N. Gregersen, et al., "Gas Chromatographic Mass Spectrometric Identification of N-Dicarboxylmonoglycines", Biomedical Mass Spectrometry, vol. 5, No. 1, pp. 80-83, 1978.

L. Guan, et al., "Synthesis and Anticonvulsant Activity of N-(2-Hydroxy-ethyl)amide Derivatives", Arch. Pharm. Chem. Life Sci. vol. 342, pp. 24-40, 2009.

V. Gududuru, et al., "Synthesis and biological evaluation of novel cytotoxic phospholipids for prostate cancer", Bioorganic & Medicinal Chemisty Letters, vol. 14, pp. 4919-4923, 2004.

C. Leschke, et al., "Alkyl-Substituted Amino Acid Amides and Analogous Di- and Triamines: New Non-Peptide G Protein Activators", Journal of Medicinal Chemistry, vol. 40, pp. 3130-3139, 1997.

A. Leydet, et al., "Polyanion Inhibitors of Human Immunodeficiency Virus and other Viruses, Part 2. Polymerized Anionic Surfactants Derived from Amino Acids and Dipeptides", Journal of Medicinal Chemistry, vol. 39, No. 8, pp. 1626-1634, 1996.

R. H. Mazur, et al., "Structure-Taste Relationships of Aspartic Acid Amides", Journal of Medicinal Chemistry, vol. 13, No. 6, pp. 1217-1221, 1970.

R. C. McKellar, et al., "Antimicrobial activity of fatty N-acylamino acids against Gram-positive foodborne pathogens", Food Microbiology, vol. 9, pp. 67-76, 1992.

C. Menozzi-Smarrito, et al., "Synthesis and Evaluation of New Alkylamides Derived from a-Hydroxysanshool, the Pungent Molecule in Szechuan Pepper", Journal of Agricultural and Food Chemistry, vol. 57, pp. 1982-1989, 2009.

A. Pal, et al., "Molecular mechanism of physical gelation of hydrocarbons by fatty acid amides of natural amino acids", Tetrahedron, vol. 63, pp. 7334-7348, 2007.

Tortoriello, "Targeted Lipidomics in *Drosophila melanogaster* Identifies Novel 2-Monoacylglycerols and N-acyl Amides", vol. 8, Issue 000.7, pp. 1-10, Jul. 2013, www.plosone.org.

Rigo, et al., "Studies on Pyrrolidinones. Synthesis of some N-Fatty Acylpyroglutamic Acids", J. Heterocyclic Chem., vol. 32, pp. 1489-1491, 1995, XP-002224102.

XP-002699514, WPI/Thomson database English abstract of JPH08103242.

International Search Report for related application PCT/US2013/034342 dated Jul. 12, 2013.

XP-002727889, WPI/Thomson database English abstract of CN101597239.

E. Piera, et al., "Qualitative and Quantitative analysis of new alkyl arginine surfactants by high-performance liquid chromatoghraphy and capillary electrophoresis", Journal of Chromatography A, vol. 852, pp. 499-506, 1999.

S. Y. Mhaskar, et al., "Synthesis of N-Acyl Amino Acids and Correlation of Structure with Surfactant Properties of Their Sodium Salts", JAOCS, vol. 67, No. 12, pp. 1015-1019, 1990.

C. L. Penney, et al., "Further studies on the adjuvanticity of stearyl tyrosine and amide analogues", Vaccine, vol. 12, No. 7, pp. 629-632, 1994.

C. W. Phoon, et al., "Isolation and total synthesis of gymnastatin N, a POLO-like kinase 1 active constituent from the fungus Arachniotus punctatus", Tetrahedron, vol. 60, pp. 11619-11628, 2004.

C. M. Ranger, et al.,"Mass spectral characterization of fatty acid amides from alfalfa trichomes and their deterrence against the potato leafhopper", Phytochemistry, vol. 66, pp. 529-541, 2005.

M. Schlitzer, et al., "Design, Synthesis and Early Structure-Activity Relationship of Farnesyltransferase Inhibitors Which Mimic Both the Peptidic and the Prenylic Substrate", Bioorganic & Medicinal Chemisty , vol. 8, pp. 1991-2006, 2000.

S. Tadashi, et al., "Aliphatic Acylamino Acids", Pharm. Society Japan, vol. 86, No. 10, pp. 967-972, 1966, Japan.

K. Takao, et al., "Studies on Inhibition of Enzymatic Arginyltransfer Reaction", Chem. Pharm. Bull. vol. 46, No. 7, pp. 1169-1172, 1998, Japan.

C. Toniolo, et al., "Effect of Na-acyl Chain Length on the Membrane-Modifying Properties of Synthetic Analogs of the Lipopeptaibol Trichogin GA IV", Journal of American Chemical Society, vol. 118, pp. 4952-4958, 1996.

K. Watanabe, et al., "Pharmacological Effects in Mice of Anandamide and Its Related Fatty Acid Ethanolamides, and Enhancement of Cataleptogenic Effect of Anandamide by Phenylmethylsulfonyl Fluoride", Bio. Pharm. Bull., vol. 22, No. 4, pp. 366-370, 1999.

A. Kolokouris, et al., "Studies on Pyrrolidinones, Synthesis of some N-Fatty Acylpyroglutamic Acids", J. Heterocyclic Chem., vol. 32, pp. 1489-1492, 1995.

M. Saito, et al., "Sythesis and Inhibitory Activity of Acyl-Peptidyl-Pyrrolidine Derivatives Toward Post-Proline Cleaving Enzyme; A Study of Subsite Specificity", Journal of Enzyme Inhibition, vol. 5, pp. 51-75, 1991, United Kingdom.

ORGANIC COMPOUNDS HAVING TASTE-MODIFYING PROPERTIES

This application is a continuation of U.S. application Ser. No. 14/916,846, filed Mar. 4, 2016, now abandoned. U.S. application Ser. No. 14/916,846 is a 371 of PCT/EP2013/070540, filed Oct. 2, 2013.

This disclosure relates to flavour modification and to compounds useful in modifying flavours.

The addition of flavours to comestible products, that is, products taken orally either for ingestion (such as foodstuffs, confectionery and beverages) or for spitting out (such as toothpastes and mouthwashes) is a long-established practice. The taste of flavours may be modified by the addition of other flavor ingredients, this generally falling within the skill of the flavourist.

More recently, there has been a desire to modify flavours by the addition of materials that are not in themselves standard flavor ingredients, that is, they do not possess a desirable taste, if any, to be suitable as flavor ingredient, but modify the flavour in some desirable way when used in very low concentrations. Some examples of these include;

Flavour boosters. These boost a flavour or some aspect of a flavour. For example, a sweetness booster may be added to a comestible product to provide the same level of sweetness with a reduced sugar content. Salt boosting is another category of such boosting. This has become very important in the production of health and dietary foods, where reduced levels of salt and/or sugar are desirable.

Off-taste maskers. It is well known that certain desirable flavour ingredients have the disadvantage of also providing an undesirable off-taste. One example is the "metallic" off-taste sometimes associated with some high-intensity sweeteners. Maskers can block these off-tastes and allow the full desired flavour effect to be realised without the disadvantages.

Mouthfeel boosters. Although not strictly a flavour characteristic, mouthfeel can add—or detract—considerably from a comestible composition. An undesirable mouthfeel can be seriously disadvantageous to an otherwise desirably-flavoured composition.

It is an additional desire of the industry to create flavours that capture natural, authentic flavour more fully in mass-manufactured comestible compositions, especially foodstuffs and beverages. For example, it is often desirable to make an orange-flavoured drink taste as close as possible to fresh-squeezed orange juice. It is generally known that, in the preparation of commercial orange-flavoured drinks, much of the authentic orange flavour is unavoidably lost. This is true of a wide variety of mass-manufactured foodstuffs and beverages.

It has now been found that the addition of certain compounds to flavour-containing comestible compositions can desirably modify the flavours therein in one or more of the abovementioned ways, resulting in compositions with more consumer appeal. There is therefore provided a method of modifying the taste of a comestible composition comprising at least one flavor co-ingredient, comprising the incorporation therein of a flavour-modifying proportion of a compound of formula (I) or edible salts thereof,

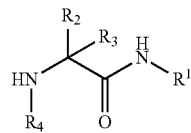

wherein $R^1$ is selected from $C_6$-$C_{20}$ alkyl, and $C_9$-$C_{25}$ alkenyl, and
i) $R^3$ and $R^4$ are hydrogen and $R^2$ the residue of a proteinogenic amino acid;
ii) $R^2$ and $R^3$ are methyl and $R^4$ is hydrogen; or $R^4$ is hydrogen and $R^2$ and $R^3$ form together with the carbon atom to which they are attached cyclopropyl;
iii) $R^2$ is hydrogen, and $R^3$ and $R^4$ together are —$CH_2$—$CH_2$—$CH_2$—.

The proteinogenic amino acids, having the generic structure of formula (II)

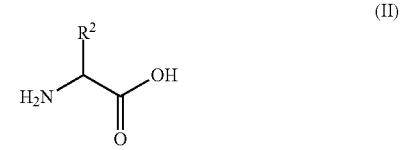

are selected from alanine (Ala; $R^2$=methyl), cysteine (Cys; $R^2$=$CH_2$—SH), aspartic acid (Asp; $R^2$=$CH_2$—C(O)O$^-$), phenylalanine (Phe; $R^2$=$CH_2$-phenyl), glutamic acid (Glu; $R^2$=$CH_2$—$CH_2$—C(O)O$^-$), histidine (His; $R^2$=$CH_2$-imidazol), isoleucine (Ile; $R^2$=but-2-yl), lysine (Lys; $R^2$=$(CH_2)_4NH_3^+$), leucine (Leu; $R^2$=isobutyl), methionine (Met; $R^2$=$(CH_2)_2$—S—$CH_3$), asparagines (Asn; $R^2$=$CH_2C(O)NH_2$), glutamine (Gln; $R^2$=$(CH_2)_2C(O)NH_2$), arginine (Arg; $R^2$=$(CH_2)_3NHC(NH_2)^+NH_2$), serine (Ser; $R^2$=$CH_2OH$), threonine (Thr; $R^2$=$CH(OH)CH_3$), valine (Val; $R^2$=isopropyl), tryptophan (Trp; $R^2$=CH2-1H-indole), tyrosine (Tyr; $R^2$=$CH_2$-phenol), and glycine (Gly; $R^2$=H).

As used in relation to compounds of formula (I), unless otherwise indicated, "alkyl" refers to linear and branched $C_6$-$C_{20}$alkyl, preferably to $C_8$-$C_{18}$ alkyl (e.g. $C_9$, $C_{10}$, $C_{11}$, $C_{13}$, $C_{14}$, $C_{15}$, $C_{16}$, $C_{17}$);

"alkenyl" refers to linear and branched $C_9$-$C_{25}$ alkenyl, including $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, and $C_{24}$ alkenyl, comprising 1-6 (e.g. 2, 3, 4, or 5 double bonds).

Edible salts include those typically employed in the food and beverage industry and include chlorides, sulphates, phosphates, gluconates, sodium, citrates, carbonates, acetates and lactates.

Non-limiting examples are compounds of formula (I) wherein $R^1$ is selected from $C_8$, $C_{10}$, $C_{12}$, $C_{14}$, $C_{16}$, $C_{18}$, $C_{20}$ linear alkyl.

Further non-limiting examples are compounds of formula (I) wherein $R^1$ is selected from $C_{10}$, $C_{12}$, $C_{14}$, $C_{16}$, $C_{18}$, $C_{20}$, $C_{22}$, $C_{24}$, $C_{26}$ linear alkenyl, comprising 1-6 (e.g. 2, 3, 4 or 5 double bonds), preferably in cis-configuration.

Further non-limiting examples are compounds of formula (I) wherein $R^3$ is hydrogen.

In one embodiment $R^1$ is selected from linear $C_x$-$C_y$ alkenyl wherein x+y is an even number from 10-24 (e.g. 12, 14, 16, 18, 20, 22) comprising 1, 2 or 3 double bonds either in cis and/or trans configuration, such as —CH$_2$—(CH$_2$)$_7$CH=CH(CH$_2$)$_3$CH$_3$; —CH$_2$—(CH$_2$)$_7$CH=CH(CH$_2$)$_5$CH$_3$; —CH$_2$—(CH$_2$)$_4$CH=CH(CH$_2$)$_8$CH$_3$; —CH$_2$—(CH$_2$)$_7$ CH=CH(CH$_2$)$_7$CH$_3$; —CH$_2$—(CH$_2$)$_9$CH=CH(CH$_2$)$_5$CH$_3$; —CH$_2$—(CH$_2$)$_7$CH=CHCH$_2$CH=CH(CH$_2$)$_4$CH$_3$; and —CH$_2$—(CH$_2$)$_7$CH=CHCH$_2$CH=CHCH$_2$CH=CHCH$_2$CH$_3$.

Further non-limiting examples are compound of formula (I) wherein $R^3$ is hydrogen, $R^2$ the residue of a proteinogenic amino acid, and $R^1$ is selected from linear $C_x$-$C_y$ alkenyl wherein x+y is an even number from 10-26 (including 12, 14, 16, 18, 20, 22, 24) comprising 1, 2 or 3 double bonds, preferably in cis-configuration.

Further non-limiting examples are compounds of formula (I) selected from
2-amino-4-(methylthio)-N-octadecylbutanamide (Ex. 1);
2-amino-4-methyl-N-octadecylpentanamide (Ex. 2);
N-octadecylpyrrolidine-2-carboxamide (Ex. 3); 4-amino-N-octadecylbutanamide (Ex 4);
1-amino-N-octadecylcyclopropanecarboxamide (Ex 5);
(Z)-4-amino-N-(octadec-9-en-1-yl)butanamide (Ex 6); and
N-hexadecyl 4-aminobutyramide (Ex. 7).

The compounds of formula (I) can be prepared according to methods known in the art, using commercially available starting materials, reagents and solvents. The compounds of formula (I) may be prepared, for example, by first activating the carboxylic acid group of the corresponding BOC-protected amino acid with chloro ethyl formate followed by reaction with the fatty amine. In a second step the BOC group (=t-butyloxycarbonyl group) is removed to obtain the desired compound.

The compounds of formula (I), as hereinabove described, impart remarkable organoleptic properties to comestible products to which they are added. In particular, they impart highly intense, authentic and harmonious flavour, and a roundness and fullness to comestible products containing them.

This finding was all the more surprising considering that when applicant tasted the compounds in dilute aqueous solution, they exhibited a disappointing, faintly fatty taste profile. As such, they appeared to be quite unsuitable for use in flavour applications. Only their combination with flavour co-ingredients and the judicious selection of their usage levels was it possible to discover the remarkable organoleptic properties of these compounds. Their effect on comestible products is quite unusual in that they actually complement, lift or accentuate the essential or authentic flavour and mouth feel characteristics of the foods or beverages in which they are incorporated. Accordingly, the compounds of the present invention find utility in a broad spectrum of comestible products in the food and beverage industry, as well as in health and wellness.

Accordingly, there is provided in another of its aspects, a method of conferring flavour and/or mouthfeel to, or improving taste and/or mouthfeel of a comestible composition, which method comprises adding to said composition a compound of formula (I) defined herein.

The remarkable organoleptic effects are observed when the compounds of formula (I) are incorporated into a comestible composition containing one or more flavour co-ingredients.

Accordingly, there is provided in a further embodiment a comestible composition, comprising an edible composition base, at least one flavour co-ingredient and a flavour-modifying proportion of a compound according to formula (I), as defined herein.

By "flavour co-ingredient" is meant an ingredient that is able to contribute or impart or modify in a positive or pleasant way to the taste of a comestible composition, for example, sugars, fats, salt (e.g. sodium chloride), MSG (monosodium glutamate), calcium ions, phosphate ions, organic acids, proteins, purines, flavours, and mixtures thereof. Flavour co-ingredients can also include salt tastants, umami tastants, and savoury flavour compounds.

By "taste" is meant those sensations that are perceived through the oral cavity, including, salty, sweet, sour, bitter, and umami.

Non limiting examples of flavor co-ingredients include: NaCl, KCl, MSG, guanosine monophosphate (GMP), inosin monophospahte (IMP), ribonucleotides such as disodium inosinate, disodium guanylate, N-(2-hydroxyethyl)-lactamide, N-lactoyl-GMP, N-lactoyl tyramine, gamma amino butyric acid, allyl cysteine, 1-(2-hydroxy-4-methoxyphenyl)-3-(pyridine-2-yl)propan-1-one, arginine, potassium chloride, ammonium chloride, succinic acid, N-(2-methoxy-4-methyl benzyl)-N'-(2-(pyridin-2-yl)ethyl) oxalamide, N-(heptan-4-yl)benzo(D)(1,3)dioxole-5-carboxamide, N-(2,4-dimethoxybenzyl)-N'-(2-(pyridin-2-yl)ethyl) oxalamide, N-(2-methoxy-4-methyl benzyl)-N'-2(2-(5-methyl pyridin-2-yl)ethyl) oxalamide, cyclopropyl-E,Z-2,6-nonadienamide.

In a particular embodiment, sugars are present in amounts of 0.001% to 90%, more particularly 0.001% to 50%, still more particularly 0.001% to 20% based on the total weight of the comestible composition.

For example sugars (e.g. sweetener such as Sucrose, High Fructose Corn Syrup, Fructose and Glucose; high intensity, non-nutritive sweeteners such as Aspartame Acesulfame K, Sucralose, Cyclamate, Na+ Saccharin, Neotame, Rebaudioside A and/or other stevia based sweeteners) may be present in beverages up to 20% based on the total weight of the comestible composition.

Examples of sweetener concentration conventionally present in beverages are: Carbonated Soft drink: <1% to 15% sweetener; Still beverages (non-alcoholic): <1% to 15% sweetener; Juice beverages; <1% to 15% sweetener; Powdered Soft drinks: <1% to 20% sweetener; Liquid concentrates: <1% to 20% sweetener; Alcoholic beverages: <1% to 40% sweetener; Functional beverages: <1% to 20% sweetener; Coffee based beverages: <1% to 15% sweetener; and Tea based beverages: <1% to 15% sweetener.

In a particular embodiment, fats are present in amounts of 0.001% to 100%, more particularly 0.001% to 80%, more particularly 0.001% to 30%, still more particularly 0.001% to 5% based on the total weight of the comestible composition.

In a particular embodiment, salt (e.g. sodium chloride) is present in amounts of 0.001% to 20%, more particularly 0.001% to 5% based on the total weight of the comestible composition.

In a particular embodiment, MSG is present in amounts of 0.001% to 2% based on the total weight of a comestible composition.

In a particular embodiment, calcium is present in amounts of 0.001% to 50% more particularly 0.001% to 20%, still more particularly 0.001% to 1% based on the total weight of the comestible composition.

In a particular embodiment, organic acids are present in amounts of 0.001% to 10%, more particularly 0.001% to 7% based on the total weight of the comestible composition. Types of organic acids include citric, malic, tartaric, fumaric, lactic, acetic and succinic. Types of comestible products containing organic acids include beverages, such as carbonated soft drink beverages, still beverages, Juices, powdered soft drinks, liquid concentrates, alcoholic beverages and functional beverages.

In a particular embodiment, phosphorus is present in an amount up to 0.5% by weight of the comestible composition. Typically phosphorus will be present as a phosphate or as phosphoric acid.

In a particular embodiment, purines are present in an amount up to 0.5% by weight of a comestible composition. The term "purines" include ribonucleotides such as IMP and GMP.

In a particular embodiment, flavours are present in an amount up to 15% by weight, for example in an amount from 0.01-15% by weight (e.g. 10-15% by weight in a snack foods, 0.1-0.5% by weight in a savoury food product, 0.01-0.1% by weight in sweet products and dairy product), of the comestible composition.

All manner of flavours may be employed in a composition according to the present invention, including, but not limited to natural flavours, artificial flavours, spices, seasonings, and the like. Flavours include synthetic flavour oils and flavouring aromatics and/or oils, oleoresins, essences, distillates, and extracts derived from plants, leaves, flowers, fruits, and so forth, and combinations comprising at least one of the foregoing.

Flavour oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil; useful flavouring agents include artificial, natural and synthetic fruit flavours such as vanilla, and citrus oils including lemon, orange, lime, grapefruit, yazu, sudachi, and fruit essences including apple, pear, peach, grape, blueberry, strawberry, raspberry, cherry, plum, prune, raisin, cola, guarana, neroli, pineapple, apricot, banana, melon, apricot, ume, cherry, raspberry, blackberry, tropical fruit, mango, mangosteen, pomegranate, papaya and the like.

Additional exemplary flavours imparted by a flavour composition include a milk flavour, a butter flavour, a cheese flavour, a cream flavour, and a yogurt flavour; a vanilla flavour; tea or coffee flavours, such as a green tea flavour, an oolong tea flavour, a tea flavour, a cocoa flavour, a chocolate flavour, and a coffee flavour; mint flavours, such as a peppermint flavour, a spearmint flavour, and a Japanese mint flavour; spicy flavours, such as an asafetida flavour, an ajowan flavour, an anise flavour, an angelica flavour, a fennel flavour, an allspice flavour, a cinnamon flavour, a chamomile flavour, a mustard flavour, a cardamom flavour, a caraway flavour, a cumin flavour, a clove flavour, a pepper flavour, a coriander flavour, a sassafras flavour, a savoury flavour, a Zanthoxyli Fructus flavour, a perilla flavour, a juniper berry flavour, a ginger flavour, a star anise flavour, a horseradish flavour, a thyme flavour, a tarragon flavour, a dill flavour, a capsicum flavour, a nutmeg flavour, a basil flavour, a marjoram flavour, a rosemary flavour, a bayleaf flavour, and a wasabi (Japanese horseradish) flavour; a nut flavour such as an almond flavour, a hazelnut flavour, a macadamia nut flavour, a peanut flavour, a pecan flavour, a pistachio flavour, and a walnut flavour; alcoholic flavours, such as a wine flavour, a whisky flavour, a brandy flavour, a rum flavour, a gin flavour, and a liqueur flavour; floral flavours; and vegetable flavours, such as an onion flavour, a garlic flavour, a cabbage flavour, a carrot flavour, a celery flavour, mushroom flavour, and a tomato flavour.

In some embodiments, said flavour composition include aldehydes and esters such as cinnamyl acetate, cinnamaldehyde, citral diethylacetal, dihydrocarvyl acetate, eugenyl 49 formate, p-methylamisol, and so forth can be used. Further examples of aldehyde flavourings include acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavours), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), and the like.

Further examples of other flavours can be found in "Chemicals Used in Food Processing", publication 1274, pages 63-258, by the National Academy of Sciences.

In preparing the comestible composition, the compounds of formula (I) may be employed in any physical form. They may be used in neat form, in the form of a stock solution; they may be used in the form of an emulsion; or they may be used in a powder form. If the compounds of formula (I) are presented in the form of a powder, the powder form may be prepared by subjecting a liquid formulation containing a compound of formula (I) to a dispersive evaporation process. The liquid formulation may comprise a solution, suspension or emulsion comprising the compound of formula (I). The liquid formulation may contain other ingredients such as a carrier material and/or an adjuvant suitable for flavour compositions.

In a further embodiment the compounds of formula (I) may be admixed with a flavour co-ingredient, in particular with flavours before incorporated into an edible composition base.

Thus there is provided in a further aspect a flavour composition comprising a compound of formula (I) as herein defined and at least one flavour co-ingredient, in particular flavours, and optionally a carrier material and/or an adjuvant suitable for flavour compositions as described more fully below.

The carrier material may be employed to encapsulate or to entrap in a matrix a compound of formula (I), or composition, in particular a flavour composition, containing a compound of formula (I). The role of the carrier material may be merely that of a processing aid or a bulking agent, or it might be employed to shield or protect the other components from the effects of moisture or oxygen or any other aggressive media. The carrier material might also act as a means of controlling the release of flavour from the product when consumed.

Carrier materials may include mono, di- or trisaccharides, natural or modified starches, hydrocolloids, cellulose derivatives, polyvinyl acetates, polyvinylalcohols, proteins or pectins. Example of particular carrier materials include sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylmethyl cellulose, derivatives and mixtures thereof. Of course, the skilled address with appreciate that the cited materials are hereby given by way of example and are not to be interpreted as limiting the invention.

By "flavour adjuvant" is meant an ingredient capable of imparting additional added benefit to compositions of the present invention such as a colour, light resistance, chemical stability and the like. Suitable adjuvants include solvents (including water, alcohol, ethanol, triacetine, oils, fats, vegetable oil and miglyol), binders, diluents, disintegrating agents, lubricants, colouring agents, preservatives, antioxidants, emulsifiers, stabilisers, anti-caking agents, and the like. In a particular embodiment, the flavour composition comprises an anti-oxidant. Said anti-oxidants may include vitamin C, vitamin E, rosemary extract, antrancine, butylated hydroxyanisole (BHA) and butylated hydroxytoluene (BHT).

Examples of such carriers or adjuvants for flavour compositions may be found in for example, "Perfume and Flavour Materials of Natural Origin", S. Arctander, Ed., Elizabeth, N.J., 1960; in "Perfume and Flavour Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

Other suitable and desirable ingredients of flavour compositions are described in standard texts, such as "Handbook of Industrial Chemical Additives", ed. M. and I. Ash, 2nd Ed., (Synapse 2000).

Flavour compositions according to the present invention may be provided in any suitable physical form. For example, they may be in the form of oils, emulsions or dispersions in a hydrous liquid or organic liquid suitable for use in comestible products, or solid form, such as powders.

If the flavour compositions are to be provided in the form of a powdered composition, they may be prepared by dispersive evaporation techniques generally known in the art, such as spray drying.

Accordingly, in a further embodiment there is provided a method of forming a powder composition, comprising the steps of providing a liquid composition comprising a compound of the formula (I) and one or more optional ingredients selected from at least one flavour co-ingredient, a carrier material and an adjuvant, and dispersively evaporating said liquid composition to form a powder composition.

In this manner, a compound of formula (I) or a flavour composition comprising said compound may be presented in a powder form.

The liquid composition used in the preparation of a powder may be in the form of a solution, emulsion, dispersion or slurry. The liquid may contain water, and/or an organic liquid, such as ethanol, glycerol, triacetine, miglyol (MCT) that is acceptable for use in comestible products.

Powder compositions may be prepared according to methods and apparatus known in the art for producing powders on an industrial scale. A particularly suitable method is spray drying. Spray drying techniques and apparatus are well known in the art and need no detailed discussion herein. The spray drying techniques, apparatus and methods described in US2005/0031769 and US2013/0022728, as well as those techniques, apparatus and methods described in those documents are suitable for producing powder compositions and are herein incorporated by reference in their entirety.

As stated hereinabove, compounds of formula (I) or flavour compositions containing such compounds can be incorporated into comestible products, and a comestible composition or a flavor composition containing such a compound of formula (I) form another aspects of the present invention.

The term "comestible composition" refers to products for consumption by a subject, typically via the oral cavity (although consumption may occur via non-oral means such as inhalation), for at least one of the purposes of enjoyment, nourishment, or health and wellness benefits. Comestible products may be present in any form including, but not limited to, liquids, solids, semi-solids, tablets, capsules, lozenges, strips, powders, gels, gums, pastes, slurries, syrups, aerosols and sprays. The term also refers to, for example, dietary and nutritional supplements. Comestible products include compositions that are placed within the oral cavity for a period of time before being discarded but not swallowed. It may be placed in the mouth before being consumed, or it may be held in the mouth for a period of time before being discarded. A comestible composition as herein above defined includes compositions whose taste is modified in the manner described herein by the addition of compounds of formula (I).

Broadly, the comestible composition includes, but is not limited to foodstuffs of all kinds, confectionery products, baked products, sweet products, savoury products, fermented products, dairy products, beverages and oral care products.

In a particular embodiment the term "comestible products" refers to products for consumption by a subject, typically via the oral cavity (although consumption may occur via non-oral means such as inhalation), for one of the purposes of enjoyment or nourishment.

In a more particular embodiment the term "comestible products" refers to products for consumption by a subject, typically via the oral cavity (although consumption may occur via non-oral means such as inhalation), for the purpose of enjoyment. Still more particularly, the term refers to foodstuffs and beverages.

Exemplary foodstuffs include, but are not limited to, chilled snacks, sweet and savoury snacks, fruit snacks, chips/crisps, extruded snacks, tortilla/corn chips, popcorn, pretzels, nuts, other sweet and savoury snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, dried food, dessert mixes, sauces, dressings and condiments, herbs and spices, spreads, jams and preserves, honey, chocolate spreads, nut-based spreads, and yeast-based spreads.

Exemplary confectionery products include, but are not limited to, chewing gum (which includes sugarized gum, sugar-free gum, functional gum and bubble gum), centerfill confections, chocolate and other chocolate confectionery, medicated confectionery, lozenges, tablets, pastilles, mints, standard mints, power mints, chewy candies, hard candies, boiled candies, breath and other oral care films or strips, candy canes, lollipops, gummies, jellies, fudge, caramel, hard and soft panned goods, toffee, taffy, liquorice, gelatin candies, gum drops, jelly beans, nougats, fondants, combinations of one or more of the above, and edible flavour compositions incorporating one or more of the above.

Exemplary baked products include, but are not limited to, alfajores, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savoury biscuits and crackers, bread substitutes, Exemplary sweet products include, but are not limited to, breakfast cereals, ready-to-eat ("rte") cereals, family breakfast cereals, flakes, muesli, other ready to eat cereals, children's breakfast cereals, hot cereals, Exemplary savoury products include, but are not limited to, salty snacks (potato chips, crisps, nuts, tortilla-tostada, pretzels, cheese snacks, corn snacks, potato-snacks, ready-to-eat popcorn, microwaveable popcorn, pork rinds, nuts, crackers, cracker snacks, breakfast cereals, meats, aspic, cured meats (ham, bacon), luncheon/breakfast meats (hotdogs, cold cuts, sausage), tomato products, margarine, peanut butter, soup (clear, canned, cream, instant, UHT), canned vegetables, pasta sauces.

Exemplary dairy products include, but are not limited to, cheese, cheese sauces, cheese-based products, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavoured, functional and other condensed milk, flavoured milk drinks, dairy only flavoured milk drinks, flavoured milk drinks with fruit juice, soy milk, sour milk drinks, fermented dairy drinks, coffee whiteners, powder milk, flavoured powder milk drinks, cream, yoghurt, plain/natural yoghurt, flavoured yoghurt, fruited yoghurt, probiotic yoghurt, drinking yoghurt, regular drinking yoghurt, probiotic drinking yoghurt, chilled and shelf-stable desserts, dairy-based desserts, soy-based desserts.

Exemplary beverages include, but are not limited to, flavoured water, soft drinks, fruit drinks, coffee-based drinks, tea-based drinks, juice-based drinks (includes fruit and vegetable), milk-based drinks, gel drinks, carbonated or non-carbonated drinks, powdered drinks, alcoholic or non-alcoholic drinks.

Exemplary fermented foods include, but are not limited to, Cheese and cheese products, meat and meat products, soy and soy products, fish and fish products, grain and grain products, fruit and fruit products.

The compounds of formula (I), when added to a flavour composition and/or a comestible composition, may modify any aspect of the temporal profile of taste and/or mouthfeel of a comestible composition.

Compounds of formula (I) or flavour compositions containing same may be added to comestible products in widely carrying amounts. The amount will depend on the nature of the comestible composition to be flavoured, and on the desired effect, as well as on the nature of the ingredients present in said composition. In order to obtain the remarkable beneficial effects attributed to the presence of the compounds of formula (I), the flavour composition should be employed in amounts such that the compounds of formula (I) are present in amounts of 1 part per billion to 10 parts per million based on the total weight of the comestible composition. Whereas amounts higher than this can be employed, the beneficial effects are considerably less apparent and undesirable off-notes can become increasingly apparent.

Interesting organoleptic effects, e.g. salt, alcohol or coolant boosting effects, in comestible products containing salt or alcohol or coolant compounds can be achieved when compounds of the formula (I) are employed at levels of 1 to 100 ppb.

Interesting organoleptic effects, for example umami boosting effects, in comestible products containing umami tastants can be achieved when compounds of the formula (I) are employed at levels of 100 to 250 ppb.

Interesting organoleptic effects, in particular mouthfeel boosting effects, in comestible products can be achieved when compounds of the formula (I) are employed at levels of 250 to 500 ppb.

Interesting organoleptic effects, e.g. fat boosting effects, in comestible products containing fats can be achieved when compounds of the formula (I) are employed at levels of 500 to 1000 ppb.

It is particularly advantageous to incorporate compounds of formula (I) into comestible products that are formed under conditions of high temperature, such as baking, frying or which are processed by heat treatments such as pasteurization or under UHT conditions. Under high preparation or processing temperatures, volatile flavour ingredients may be lost or degraded with the result that flavour intensity can be reduced and the essential and authentic flavour characteristics can be diminished. Such edible products include dairy products, snack foods, baked products, powdered soft drinks and similar dry mixes, and the like, fats and condiments, mayonnaise, dressings, soups and bouillons, and beverages.

A particularly preferred class of comestible composition according to the present invention are powdered soft drinks and similar dry mix applications. Dry mix applications are known in the art and included products in powder form that are intended to be reconstituted before consumption. They include powdered soups, powdered cake mixes, powdered chocolate drinks, instant coffees, seasonings and fonds, and the like.

Dry powders formed by dispersive evaporation processes, such as spray drying, represent a very convenient vehicle to deliver flavour oil quality flavours to comestible products.

Another particularly preferred class of comestible composition according to the present invention are snack foods. Snack foods are a category of product well known to the skilled person in the food industry. These products are described above and include, without limitation, pretzels, corn chips, potato chips, puffed products, extruded products, tortilla chips and the like. Still more particularly, the invention is concerned with low fat snack food compositions. Low fat snack food compositions contain less that 30% by weight fat, more particularly between 5 to 25% by weight of fat.

A problem with reducing fat in a snack food composition is the loss in taste and texture. Fats play an important role in the way that dough behaves during processing and greatly affect the quality, flavor and texture of ready-to-eat products. As the fat content in snack products is reduced or replaced with other ingredients (e.g., non-digestible fat, protein, fiber, gums), adverse organoleptic effects (e.g., mouth coating, drying, lack of crispness and lack of flavour) are increased. The adverse organoleptic effects result in products having reduced palatability.

Considerable efforts have been expended in devising flavour compositions to overcome the problems associated with low fat snack food products. Flavours may be applied to a snack food as topical coatings in the form of dry powders and/or as liquids (e.g., oil-based, water-based). Another approach has been to add flavour to the dough.

Despite these various approaches which have been taken to improve consumer appeal and palatability of snack foods, and particularly low fat snack foods, there is still a need for improved low-fat snack foods having coatings applied thereto with the visual appeal, flavor, and texture of full-fat snack foods.

Compounds according to formula (I) or flavour compositions containing same can be incorporated into snack foods to impart an impactful flavour and a mouthfeel with a remarkable roundness and fullness. Furthermore, the taste and mouthfeel effects can be achieved even in low fat snack foods.

Accordingly, the invention provides in another of its aspects a snack food comprising a flavour composition as hereinabove described. In a particular embodiment of the invention the snack food has a fat content of about 40% or less by weight based on the total weight of the snack food, more particularly about 30% or less, still more particularly 25% or less, more particularly still about 10% or less, still more particularly about 5% or less, still more particularly about 3% or less.

Examples of snack foods are described above and include products processed by oven baking, extrusion or frying, and which are made from potato and/or corn and/or various grains such as rice or wheat.

Another particularly preferred class of comestible composition according to the present invention is alcoholic beverages.

Applicant surprisingly found that compounds according to formula (I) incorporated into an alcoholic beverage had the effect of increasing the alcohol impact of the beverage.

Accordingly, the invention provides in another of its aspects an alcoholic beverage comprising a compound according to formula (I).

In yet another aspect of the invention there is provided a method of producing a heightened alcoholic impression in an alcoholic beverage by incorporating into said beverage a compound according to formula (I).

Compounds of formula (I) may be incorporated into said alcoholic beverage in amounts of 1 ppb to 1 ppm.

Another class of comestible products are products taken orally in the form of tablets, capsules, powders, multiparticulates and the like. Such compounds may include pharmaceutical dosage forms or nutraceutical dosage forms.

Certain groups of people have problems swallowing tablets or capsules, powders, multi-particulates and the like. This problem can be particularly pronounced in certain consumer groups, such as children and the very old or infirm. Applicant surprisingly found that compounds according to the formula (I) when taken into the oral cavity produce a pronounced salivating effect. Incorporating the compounds into these forms, particularly as part of a coating around said dosage forms can ease the swallowing process for consumers, in particular children and the old or infirm.

Accordingly, the invention provides in another of its aspects an orally administrable dosage form, in particular in the form of tablets capsules, powders or multiparticulates comprising a compound according to the formula (I).

Another preferred class of comestible composition is baked goods. Compounds of the formula (I) may be incorporated topically or in-dough. Incorporated at levels of 1 ppb to 1 ppm, the compounds of formula (I) render baked products less dry and more succulent.

Other preferred class of comestible products are caloric or non-caloric beverages containing carbohydrate sweeteners, such as sucrose, high fructose corn syrup, fructose and glucose, or high intensity, non-nutritive sweeteners such as aspartame, acesulfame K, sucralose, cyclamate, sodium saccharin, neotame, rebaudioside A, and/or other stevia-based sweeteners; as well as other optional ingredients such as juices, organic acids such as citric acid, alcohol and functional ingredients.

Incorporated at levels of 1 ppb to 10 ppm, compounds of formula (I) impart to said beverages containing sweeteners at levels of less than 1% and up to about 20%, an upfront sweetness and mouthfeel that is reminiscent of sugar.

Other preferred comestible products are savoury compositions, in particular those that are soy-based or fish-based.

Incorporated at levels of 1 ppb to 10 ppm, in a soy-based composition (such as soy sauce) or a fish-based composition (such as fish sauce) containing 5 to 40% salt, the compositions are found to exhibit strong umami tastes that are long-lasting and rich.

Another preferred comestible composition is a clouded beverage composition.

Certain beverages such as juices have relatively higher turbidity and thus have an opaque appearance. Often, it is desired that the beverage have a relatively high turbidity. This might be desirable to provide a more natural appearance to beverages with low juice content, or it might be for reasons related to masking sedimentation or "ringing" (where flavour or colour oils rise to the surface of a container during storage). Clouded beverages are usually formed by means of a clouding agent. Clouding agents are usually supplied in the form of emulsions, or the clouding agent may be part of a powdered beverage that upon reconstitution will formed an emulsion providing a permanent cloud to the beverage.

Compounds of the formula (I), in addition to their remarkable organoleptic properties, can lend stability to clouding agents and to beverage compositions containing same.

Other preferred comestible products are those compositions that are formed by a process of ripening. In food processing, it frequently occurs that a food needs to remain for a prolonged period of time and under well-defined conditions to obtain the food with the requisite and recognised quality. A commonly used term for this process is ripening. Ripening is well known in the processing of certain types of cheese, meat, soy-sauce and wine, as well as beer sausage, sauerkraut, tempeh and tofu. There are also specific steps that are carried out for specific reasons (such as water-removal, or off-note removal) that have beneficial effects on the food products. Examples of this are the conching of chocolate and the drying of noodles, vegetables and fruits. The transformations that improve the quality of the food are induced by chemical conversions, enzymatically catalysed conversions or fermentative transformations. All of these conversions are slow and therefore expensive; they are also not fully predictable or controllable.

The compounds of formula (I), having regard to their remarkable property of adding to the authentic taste characteristics of the comestible products in which they are incorporated, may be added to an edible product during its ripening process in order to reduce storage time without adversely influencing the taste quality of the ripened product.

Accordingly, in another aspect of the invention there is provided a method of ripening a product selected from the group consisting of cheese, meat, soy-sauce and wine, beer, sausage, sauerkraut, tempeh and tofu, comprising the step of ripening the product in the presence of a compound according to the formula (I).

In another aspect of the invention there is provided a method of conching chocolate, said method comprising the step of adding to the chocolate a compound according to the formula (I), or a flavour composition containing same.

The invention is now further described with reference to the following non-limiting examples. These examples are for the purpose of illustration only, and it is understood that variations and modifications can be made by one skilled in the art.

EXAMPLE 1

2-amino-4-(methylthio)-N-octadecylbutanamide a) tert-butyl (4-(methylthio)-1-(octadecylamino)-1-oxobutan-2-yl)carbamate In a 250 mL round-bottomed flask fitted with a stirrer, cooler and dropping funnel tert-butyloxycarbonyl methionine (3 g, 12.03 mmol) was dissolved in in dichloromethane (DCM; 50 ml). Solution was cooled with an ice/water bath and triethylamine (1.677 ml, 12.03 mmol) was added at a temperature of approx. 10° C.

Ethyl chloroformiate (1.306 g, 12.03 mmol) was added dropwise at 10° C.

Stirring was continued for 15 minutes while cooling. Octadecan-1-amine (3.24 g, 12.03 mmol) was added, cooling bath was removed and stirring was continued for 4 hours.

Reaction mixture stand over during the night.

Mixture was diluted with DCM, washed with a diluted aqueous solution of hydrochloric acid and with a sodiumcarbonate solution.

Organic layer was separated, dried and evaporated to yield 5 g of the title product as a white solid (Purity >95%, yield: 79%).

b) 2-amino-4-(methylthio)-N-octadecylbutanamide

In a 250 mL erlenmeyer tert-butyl (4-(methylthio)-1-(octadecylamino)-1-oxobutan-2-yl)carbamate (1 g, 1.997 mmol) was dissolved in Methanol (Volume: 100 ml).

Acetyl chloride (3.62 ml, 51.0 mmol) was added carefully while stirring.

Solution stand over during the night.

Solution was evaporated and the solid residue was washed with some acetone/ether to remove the remaining starting material.

0.4 g of title product was left with a purity >95%, yield: 45%

$^1$H NMR (600 MHz, DMSO-d$_6$) ppm 0.85 (t, J=6.70 Hz, 3 H, H—C(18)) 1.23 (m, 30 H, H—C(3, 4, 8, 6, 7, 8, 9, 10, 11, 12, 13, 14, 15, 16, 17)) 1.36-1.46 (m, 2 H, H—C(2)) 1.96 (d, J=7.22 Hz, 2 H, H—C(21) 2.05 (s, 3 H, H—C(23)) 2.47 (d, J=5.84 Hz, 2 H, H—C(22)) 3.00-3.07 (m, 1H, (H—C(1)) 3.13-3.20 (m, 1H, H—C(1)), 3.76 (t, J=6.19 Hz, 1H, H—C(20)) 8.51 (br. s., 1 H, H—N(24))

$^{13}$C NMR (150 MHz, DMSO-d$_6$) ppm 13.93 C(18)), 14.46 C(23)), 22.06 C(17)), 26.32 (C(2)), 28.13-29.10 (C(3 4, 5, 6, 7, 8, 9, 10, 1, 12, 13, 14, 15, 22) 31.07 (C(16)) 31.27 C(21)) 38.65 (C(1)), 51.69 C(C20)) 168.03 C(19))

EXAMPLE 2

2-amino-4-methyl-N-octadecylpentanamide

According to the same procedure of Example 1, 2-amino-4-methyl-N-octadecylpentanamide was prepared from leucine and octadecyl amine in a yield of 47%.

$^1$H NMR (600 MHz, DMSO-d$_6$) δ ppm 0.63-0.95 (m, 9 H) 1.05-1.29 (m, 30 H) 1.40 (br. s., 2 H) 1.55 (d, J=6.87 Hz, 3 H) 2.82-3.09 (m, 1 H) 3.09-3.21 (m, 1 H) 3.52-3.77 (m, 1 H) 3.82 (br. s., 4 H) 8.68 (s, 1 H)

$^{13}$C NMR (151 MHz, DMSO-d$_6$) δ ppm 13.90 (s, 1 C) 22.08 (s, 1 C) 22.28 (s, 1 C) 22.40 (s, 1 C) 23.72 (s, 1 C) 26.32 (s, 1 C) 28.70 (s, 1 C) 29.00 (s, 1 C) 29.04 (s, 1 C) 31.29 (s, 1 C) 38.57 (s, 1 C) 40.20 (s, 1 C) 50.97 (s, 1 C) 168.49 (s, 1 C)

EXAMPLE 3

N-octadecylpyrrolidine-2-carboxamide

According to the same procedure of Example 1, N-octadecylpyrrolidine-2-carboxamide was prepared from proline and octadecyl amine in a yield of 78%.

$^1$H NMR (600 MHz, DMSO-d$_6$) δ ppm 0.88 (t, J=6.87 Hz, 3 H) 1.05-1.40 (m, 31 H) 1.50 (d, J=6.87 Hz, 2 H) 1.89-2.13 (m, 3 H) 2.31-2.51 (m, 1 H) 2.85-3.28 (m, 5 H) 3.34 (t, J=6.87 Hz, 2 H) 4.34 (s, 1 H) 8.44-8.53 (m, 1H)

$^{13}$C NMR (151 MHz, DMSO-d$_6$) δ ppm 13.08 (s, 1 C) 21.49 (s, 1 C) 23.14 (s, 1 C) 25.77 (s, 1 C) 28.12 (s, 1 C) 28.14 (s, 1 C) 28.39 (s, 1 C) 28.44 (s, 1 C) 28.48 (s, 1 C) 29.39 (s, 1 C) 30.72 (s, 1 C) 38.60 (s, 1 C) 38.74 (s, 1 C) 38.87 (s, 1 C) 39.02 (s, 1 C) 39.15 (s, 1 C) 39.29 (s, 1 C) 39.44 (s, 1 C) 45.06 (s, 1 C) 58.27 (s, 1 C) 166.96 (s, 1 C)

EXAMPLE 4

4-amino-N-octadecylbutanamide

According to the same procedure of Example 1, 4-amino-N-octadecylbutanamide was prepared from Gamma aminobutyric acid and octadecyl amine in a yield of 23%.

$^1$H NMR (600 MHz, DMSO-d$_6$) δ ppm 0.85 (t, J=6.70 Hz, 3 H) 1.16-1.31 (m, 27 H) 1.31-1.42 (m, 2 H) 1.73 (s, 2 H) 2.15 (t, J=7.22 Hz, 2 H) 2.69-2.82 (m, 2 H) 3.01 (d, J=6.19 Hz, 3 H) 7.84-7.94 (m, 1H)

$^{13}$C NMR (151 MHz, DMSO-d$_6$) δ ppm 13.95 (s, 1 C) 22.08 (s, 1 C) 23.55 (s, 1 C) 26.43 (s, 1 C) 28.68 (s, 1 C) 28.76 (s, 1 C) 28.98 (s, 1 C) 29.01 (s, 1 C) 29.09 (s, 1 C) 31.28 (s, 1 C) 32.13 (s, 1 C) 38.49 (s, 1 C) 38.72 (s, 1 C) 171.05 (s, 1 C)

EXAMPLE 5

1-amino-N-octadecylcyclopropanecarboxamide

According to the same procedure of Example 1, 1-amino-N-octadecylcyclopropanecarboxamide was prepared from 1-amino-cyclopronae carboxylic acid and octadecyl amine in a yield of 50%.

$^1$H NMR (600 MHz, DMSO-d$_6$) ppm 0.85 (t, J=6.87 Hz, 3 H, H—C(18)) 1.18-1.29 (m, 32 H, H—C(3, 4, 5, 6, 7, 8, 9, 10, 11, 12, 13, 14, 15, 16, 17, 20, 21) 1.35 (m, 2 H, H—C(20, 21)) 3.05 (m, 2 H, H—C(1)) 7.73 (t, J=6.36 Hz 1 H, H—N(23))

$^{13}$C NMR (150 MHz, DMSO-d$_6$) ppm 12.00 (C(21, 22)), 13.94 (C(18)) 22.07 C(17)), 26.27 C(3)), 28.63-29.09 C(2, 4, 5, 6, 7, 8, 9, 10, 11, 12, 13, 14, 15), 31.27 C(16)), 34.69 C(C20)) 39.03 C(1)), 168.61 C(19))

EXAMPLE 6

(Z)-4-amino-N-(octadec-9-en-1-yl)butanamide

According to the same procedure of Example 1, (Z)-4-amino-N-(octadec-9-en-1-yl)butanamide was prepared from gamma butyric acid and and 9-octadecenyl amine in a yield of 38%.

$^1$HNMR (600 MHz, DMSO-$d_6$) δ ppm 0.85 (t, J=6.87 Hz, 1 H) 1.12-1.28 (m, 10 H) 1.28- 1.42(m, 2 H) 1.76 (quin, J=7.39 Hz, 1 H) 1.84-2.04 (m, 2 H) 2.16 (t, J=7.22 Hz, 1 H) 2.64-2.81 (m, 1 H) 3.00 (q, J=6.76 Hz, 1 H) 5.25-5.38 (m, 1 H) 7.93-8.13 (m, 1 H)

$^{13}$C NMR (151 MHz, DMSO-$d_6$) δ ppm 13.93 (s, 1 C) 22.07 (s, 1 C) 23.22 (s, 1 C) 26.45 (s, 1 C) 26.56 (s, 1 C) 26.60 (s, 1 C) 28.57 (s, 1 C) 28.61 (s, 1 C) 28.67 (s, 1 C) 28.76 (s, 1 C) 28.81 (s, 1 C) 28.84 (s, 1 C) 28.87 (s, 1 C) 29.02 (s, 1 C) 29.04 (s, 1 C) 29.07 (s, 1 C) 29.09 (s, 1 C) 29.13 (s, 1 C) 31.27 (s, 1 C) 31.92 (s, 1 C) 32.12 (s, 1 C) 38.41 (s, 1 C) 38.48 (s, 1 C) 129.62 (s, 1 C) 130.05 (s, 1 C) 170.99 (s, 1 C)

EXAMPLE 8

Mango Flavoured Beverage

A mango-flavoured beverage was prepared using a standard mango flavour (0.05% w/w), mango juice (0.18% w/w), sugar (8% w/w) and citric acid (0.1% w/w). The drinks were evaluated by a panel of experienced tasters.
   a) When 1 ppm of 1-amino-N-octadecylcyclopropanecarboxamide (Ex 5) was dosed to the mango drink the panel agreed that the drink tasted more sweet, more ripe mango, more full and more long-lasting than the reference drink.
   b) When 1 ppm of N-octadecylpyrrolidine-2-carboxamide (Ex 3) was dosed to the mango drink the panel agreed that this drink tasted more over-ripe, more sweet, and more full and had an increased mouthfeel than the reference drink.

EXAMPLE 9

Beef Bouillon

A beef bouillon was prepared using bouillon cubes obtained from a local supermarket. The drinks were evaluated by a panel of experienced tasters.
   a) When 1 ppm of 2-amino-4-(methylthio)-N-octadecylbutanamide (Ex 1) was dosed to the bouillon the panel agreed that this drink tasted more salty and more full than the reference.
   b) When 1 ppm of N-hexadecyl 4-aminobutyramide (Ex 7) was dosed to the bouillon the panel agreed that this drink tasted more salty and more umami and was more longlasting than the reference.

The invention claimed is:

1. A flavour composition comprising a flavor co-ingredient and a compound selected from: 2-amino-4-(methylthio)-N-octadecylbutanamide, 1-amino-N-octadecylcyclopropanecarboxamide, and edible salts thereof, wherein the compound exhibits an organoleptic benefit when present at a concentration of 1 ppb-10 ppm in a comestible composition, based on the weight of the comestible composition.

2. The flavour composition according to claim 1, wherein the said compound selected from: 2-amino-4-(methylthio)-N-octadecylbatanamide, 1-amino-N-octadecylcylopropanecarboxamide, or edible salt thereof exhibits a salt, alcohol or coolant boosting effect when present at a concentration of 1 ppb-100 ppb in a comestible composition, based on the weight of the comestible composition and where said comestible composition contains salt, alcohol or coolant compounds.

3. The flavour composition according to claim 1, wherein the said compound selected from: 2-amino-4-(methylthio)-N-octadecylbatanamide, 1-amino-N-octadecylcylopropanecarboxamide, or edible salt thereof exhibits umami boosting effects when present at a concentration of 100 ppb-250 ppb in a comestible composition, based on the weight of the comestible composition and where said comestible composition contains umami tastants.

4. The flavour composition according to claim 1, wherein the said compound selected from: 2-amino-4-(methylthio)-N-octadecylbutanamide, 1-amino-N-octadecylcyclopropanecarboxamide, or edible salt thereof exhibits mouthfeel boosting effects when present at a concentration of 250 ppb-500 ppb in a comestible composition, based on the weight of the comestible composition.

5. The flavour composition according to claim 1, wherein the said compound selected from: 2-amino-4-(methylthio)-N-octadecylbutanamide, 1-amino-N-octadecylcyclopropanecarboxamide, or edible salt thereof exhibits fat boosting effects when present at a concentration of 500 ppb-1000 ppb in a comestible composition, based on the weight of the comestible composition and where said comestible composition contains fats.

6. The flavour composition according to claim 1, wherein the said compound selected from: 2-amino-4-(methylthio)-N-octadecylbutanamide, 1-amino-N-octadecylcyclopropanecarboxamide, or edible salt thereof exhibits sweetness effects when present at a concentration of 1 ppb-10 ppm in a beverage composition.

7. The flavour composition according to claim 1, wherein the said compound selected from: 2-amino-4-(methylthio)-N-octadecylbutanamide, 1-amino-N-octadecylcyclopropanecarboxamide, or edible salt thereof is present at a concentration of 1 ppb-10 ppm in a soy based composition or a fish based composition.

8. A taste modifying agent comprising a compound selected from: 2-amino-4-(methylthio) -N-octadecylbutanamide, 1-amino-N-octadecylcyclopropanecarboxamide, and edible salts thereof, present in a consumable product at a concentration of 1 ppb-10 ppm based on the weight of the consumable product.

9. The taste modifying agent of claim 8, wherein when the said compound selected from: 2-amino-4-(methylthio)-N-octadecylbutanamide, 1-amino-N-octadecylcyclopropanecarboxamide or edible salt thereof, present in the consumable product at a concentration of 1 ppb-100 ppb based on the weight of the consumable product exhibits a sale, alcohol or coolant boosting effect where said consumable product contains salt, alcohol or coolant compounds.

10. The taste modifying agent of claim 8, wherein when the said compound selected from: 2-amino-4-(methylthio)-N-octadecylbutanamide, 1-amino-N-octadecylcyclopropanecarboxamide or edible salt thereof, present in the consumable product at a concentration of 100 ppb-250 ppb in the consumable product based on the weight of the consumable product exhibits umami boosting effects where the consumable product contains umami tastants.

11. The taste modifying agent of claim 8, wherein when the said compound selected from: 2-amino-4-(methylthio)-N-octadecylbutanamide, 1-amino-N-octadecylcyclopropanecarboxamide or edible salt thereof, present in the consumable product at a concentration of 250 ppb-500 ppb in the consumable product based on the weight of the consumable product, exhibits mouthfeel boosting effects.

12. The taste modifying agent of claim 8, wherein when the said compound selected from: 2-amino-4-(methylthio)-N-octadecylbutanamide, 1-amino-N-octadecylcyclopropanecarboxamide or edible salt thereof, present in the consumable product at a concentration of 500 ppb-1000 ppb exhibits fat boosting effect where the consumable product contains fats.

13. The taste modifying agent of claim 8, wherein when the said compound selected from: 2-amino-4-(methylthio)-N-octadecylbutanamide, 1-amino-N-octadecylcyclopropanecarboxamide or edible sale thereof, present in a beverage composition at a concentration of 1 ppb-10 ppm based on the weight of a beverage composition exhibits sweetness effects.

14. The taste modifying agent of claim 8, wherein when the said compound selected from: 2-amino-4-(methylthio)-N-octadecylbutanamide, 1-amino-N-octadecylcyclopropanecarboxamide or edible salt thereof, is present at a concentration of 1 ppb-10 ppm in a soy based composition or a fish based composition.

\* \* \* \* \*